United States Patent [19]

Yira et al.

[11] Patent Number: 5,139,813

[45] Date of Patent: Aug. 18, 1992

[54] METHOD FOR INDUCING FLUORESCENCE IN PARYLENE FILMS BY AN ACTIVE PLASMA

[75] Inventors: Joseph H. Yira, Amery, Wis.; William F. Beach, Bridgewater, N.J.

[73] Assignee: Union Carbide Chemicals & Plastics Technology Corporation, Danbury, Conn.

[21] Appl. No.: 590,366

[22] Filed: Sep. 28, 1990

[51] Int. Cl.$^5$ ............................................. B05D 3/06
[52] U.S. Cl. ................................... 427/8; 427/38; 430/139; 250/484.1
[58] Field of Search .................... 427/8, 38, 35; 156/272.2; 430/139; 250/473.1, 483.1, 484.1, 327.2, 302

[56] References Cited

U.S. PATENT DOCUMENTS 4,123,308 10/1978 Nowlin et al. .................. 156/272
4,590,381 5/1986 Mendelson ..................... 250/484.1
4,694,171 9/1987 Hosoi et al. .................... 250/311

FOREIGN PATENT DOCUMENTS 60-138088 7/1985 Japan .

OTHER PUBLICATIONS

Takai et al., "Luminescence from Poly(p-xylylene)", Makromol Chem., Rapid Commun. 1, (1980) pp. 17-21.
Takai et al., "Photoluminescence Study in Polymers" Jpn. J. Appl. Phys. vol. 17, No. 4, Apr. 1978 pp. 651-658.
Kochi et al, "Photoluminescence of Solid Aromatic Polymers-I poly(p-xylylene)" European Polym. J. vol. 24, No. 10 (1988) pp. 917-921.
Nowlin et al., Journal of Applied Science, vol. 25, 1619-1632 (1980).

*Primary Examiner*—Shrive Beck
*Assistant Examiner*—Roy V. King
*Attorney, Agent, or Firm*—Warren K. Volles

[57] ABSTRACT

A method is provided for inducing fluorescence in films or coatings comprised in whole or in part of parylene which involves exposure of the parylene to an active plasma. A method is also provided which utilizes plasma induced fluorescence as a means for quality control inspection of films and coatings of parylene such as those contained on electronic components or for identification and/or authentication of various articles.

28 Claims, 2 Drawing Sheets

METHOD FOR INDUCING FLUORESCENCE IN PARYLENE FILMS BY AN ACTIVE PLASMA

BACKGROUND OF THE INVENTION

1. FIELD OF THE INVENTION

This invention relates in general to a process for the treatment of parylene films and coatings. In one aspect, this invention is directed to inducing fluorescence on the surface or outer layer of parylene films and coatings, such as parylene coated electronic components, by exposure thereof to an active plasma and the utilization of such fluorescence for quality control inspection purposes. In a further aspect, this invention is directed to a process for the treatment of parylene wherein selected sites are rendered fluorescent when exposed to an active plasma utilizing certain electrically excited gases. In a still further aspect, this invention relates to articles coated in whole or in part with parylene, such as negotiable instruments, identification cards, films, disks and the like, which are caused to have certain sites of a predetermined configuration capable of fluorescing when exposed to light of the proper wavelength. The invention is also directed to a process for the removal of plasma induced fluorescence.

2. BACKGROUND OF THE RELATED ART

Parylene is a generic term applied to the class of polymers, the poly-p-xylylenes (I), which are prepared most conveniently from a dimer, a [2.2]paracyclophane (II), by the process of vapor deposition polymerization.

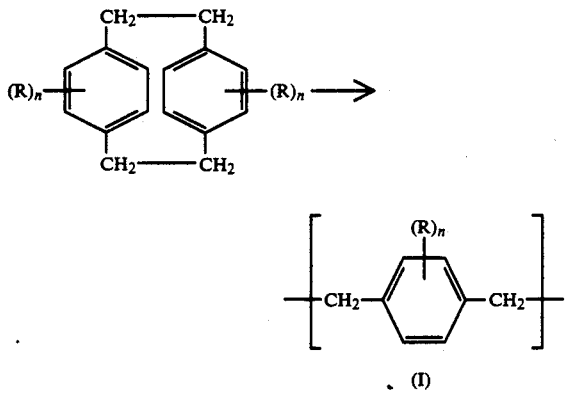

wherein R is hydrogen or chloro, with at least one R being chloro, and n has a value of from 1 to 4.

When deposited on a substrate, parylene forms a continuous, inert, transparent, conformal coating which has excellent physical, electrical and barrier properties, excellent resistance to chemical attack, and which retains these attractive properties to relatively high temperatures. Due to its ability to provide films of uniform thinness and conform to substrates of varied geometric shapes, it is ideally suited for use as a conformal coating in a wide variety of fields, particularly in the electronics industry.

The term "parylene" as employed throughout the specification and appended claims is intended to encompass not only the halogenated poly-p-xylylenes of formula (I) above, but other known parylenes containing one or more substituents on the aliphatic or aromatic portion of the recurring unit and which can be successfully rendered fluorescent by an active plasma.

The preparation of p-xylylene polymers by various routes has been reported in the patent literature. For example, in British patent number 650,947 which was granted Mar. 7, 1951, polymer formation was detected on the walls of a cooling chamber after p-xylene was vaporized and pyrolized. Those who later prepared poly-p-xylylene films by this general procedure described them as being inherently fluorescent.

Also in U.S. Pat. No. 2,719,131 which issued in Sep. 27, 1955 to E. I. DuPont de Nemours and Company there is disclosed a process for preparing poly-p-xylylene wherein the vapors of p-xylene gas were pyrolized in the presence of chlorine gas.

The preparation of para-xylylene polymers was also disclosed in U.S. Pat. No. 3,342,754 which issued on Sep. 19, 1967 to William Franklin Gorham and is assigned to Union Carbide Corporation. In this reference it is indicated that true linear homopolymers of para-xylylene could be produced in nearly quantitative yields by heating a cyclo-di-paraxylylene having up to six aromatic nuclear substituent groups to a temperature between 450° C. and 700° C. for a time sufficient to cleave substantially all of the dipara-xylylene into vaporous para-xylylene monomer and cooling the vaporous monomer to a temperature below its ceiling condensation temperature. Moreover, the higher purity poly-p-xylylene films prepared by the method of Gorham are substantially non fluorescent. The fluorescence reported in films prepared by earlier methods are presently thought to result from impurities introduced by the process.

As indicated above, prior to the present invention a wide variety of references have been available in the literature disclosing the preparation and use of poly-p-xylylene. One of the main utilities has been, and continues to be, its use as a conformal coating for a variety of articles, such as electronic circuit boards, and the like.

Parylene's use as a conformal coating for military circuit boards was recognized early, and its inclusion among the electrical insulation compounds qualifiable under the military specification governing coatings for printed circuit assemblies (MIL-I-46058) was a first order of business upon public announcement of the product in 1965. In the course of events, users of conventional coatings found that inspection of the coated board or assembly for holidays or pinholes would be greatly facilitated by the inclusion of a fluorescent dye in the otherwise clear and colorless coatings. The fluorescence from the dye would render the coated areas identifiable under an inspectors black light, but would otherwise would not be noticed. As the military requirements evolved, it became necessary for the coating manufacturer to provide the option of a fluorescent version of each coating at the users request. For conventional coatings this requirement was easily met by adding a small amount of any one of a number of commercial brighteners.

In the parylene vapor deposition polymerization process, however, a fluorescent additive compound such as a commercial brightener could conceptually either be added to the dimer at the outset of the process, or to the finished film. The parylene film barrier properties are such that diffusion of sufficient amounts of a fluorescent additive compound, necessarily a rather large molecule, into the finished film has not yet been successfully demonstrated. This process would be analogous to a dyeing of the parylene film, which also has not been successfully demonstrated. Practical considerations would further mitigate against such post deposition addition in cases where the substrate surface is convoluted, and especially when uniform distribution of fluorescence over all coated surfaces is required for the overall reliability of the inspection procedure it is intended to facilitate.

If the fluorescent additive compound is to be added to the dimer at the start of the process, it must be sufficiently volatile to pass through the process with the dimer and the product of its cleavage, the monomer, sufficiently condensible to deposit with the parylene during its deposition, and furthermore it must be sufficiently stable to survive the high temperatures of the process unchanged in its ability to create fluorescence. These conflicting requirements severely limit the field of choice among known fluorescent additives.

The first compound shown to be useful as an additive to dimer to produce fluorescence in parylene films and coatings was anthracene. Later, two members of the Calcofluor family of commercial brighteners, (Calcofluor is a trademark of American Cyanamid Co., Wayne, N. J.), known as Calcofluor White RW, RWP or SD, were shown to be still more effective as a dimer additive for producing fluorescence in parylene coatings. These compounds are 7-dialkylamino-4-methyl-coumarins, and as such are chemically different from other Calcofluor family members.

Hence, prior to the present invention, fluorescence in parylene by pre-deposition intervention was achieved specifically by the addition of a very limited number of optical brighteners to the dimer at the time of the vapor deposition polymerization process. This, of course, results in the entire parylene coating exhibiting fluorescence when methods for detecting its brightness are employed. By these processes it was not possible to create or impart fluorescence only at predetermined sites in the parylene coating.

The fluorescence produced by predeposition intervention, i.e., the addition of a fluorescent additive to the dimer at the outset of the process, while not patterned in the sense of a predetermined pattern, actually varies in intensity from place to place in the deposition chamber. The fluorescent additive is not transported through the deposition chamber as uniformly as the monomer, and tends to be deposited more heavily on substrates which were located on the line of sight from the generator nozzle. Thus, while the intensity of the fluorescence in the treated parylene article varies from place to place, for practical purposes the entire surface exhibits at least some degree of fluorescence.

Although studies had been made of the possibility of producing fluorescence by post deposition methods, no success has yet been realized in the permanent incorporation of a fluorescence additive in a parylene film by diffusion, or by a dyeing procedure. Such a procedure, if effective, would be a means of rendering selective sites of parylene coatings fluorescent. While such selective creation of fluorescent parylene coating sites may be of minimal interest in the inspection of coating quality on printed circuit assemblies, other uses abound. However, prior to the present invention, the ability to create specific sites of fluorescence in parylene coatings using an active plasma was unknown.

It should also be noted that at least one of the compounds which could be utilized to impart fluorescence to parylene films and coatings, namely anthracene, is a suspected carcinogen and hence its use should be avoided.

Additionally, when the parylene film is very thin, it will usually contain insufficient dye to be clearly detectable. If larger proportions of the dyes are employed the quality of the film or coating may be adversely effected.

Another disadvantage using additives to impart fluorescence to articles comprised in whole or in part of parylene, is that the fluorescence can not be erased. In some instances, it might be desirable to erase fluorescence from certain areas of an article coated with parylene, for example, if the fluorescence has been used for coding or part identification and revision must be made.

Accordingly, one or more of the following objects will be achieved by the practice of this invention. It is an object of this invention to provide a novel method for the treatment of parylene. Another object of this invention is to induce fluorescence in certain films and coatings by exposure to an active plasma utilizing certain gases. A further object is to provide a quality control method for inspecting certain parylene films and coatings utilizing plasma induced fluorescence. Another object of this invention is to provide a process for treating parylene wherein selective sites of fluorescence are imparted to the parylene. A further object is to provide a novel process for selectively imparting fluorescent sites to articles comprised in whole or in part of parylene. A still further object of the present invention is to provide a method for the treatment of Parylene C. Another object of this invention is to provide a process for the treatment of Parylene D. A further object is to provide articles comprised of parylene which exhibit selective sites capable of fluorescing upon exposure to certain light excitation means. Another object is to create fluorescent sites of a predetermined configuration in parylene coatings. Another object of the present invention is to use plasma induced fluorescence to detect where parylene has leaked onto unwanted areas. A still further object of the present invention is to provide articles such as negotiable instruments, currency, and the like, which have a parylene coating containing sites of a predetermined configuration which fluoresce and hence provide for identification or authentication. Another object is to induce fluorescence in parylene films and coatings which, if desired, can easily be erased using an oxygen plasma. These and other objects will become apparent to those skilled in the art in the light of the teachings herein set forth.

SUMMARY OF THE INVENTION

In its broad aspect, the invention relates to a process for inducing fluorescent sites in articles coated in whole or in part with parylene by an active plasma and using the fluorescence for the determination of areas on such articles wherein parylene is present or absent. The invention also is directed to articles coated with parylene wherein certain portions of the parylene have been rendered fluorescent by plasma treatment and hence are useful in identifying and authenticating articles. The present invention is particularly useful in maintaining quality control in the coating of various articles. In such instances it may be desirable to detect those areas where parylene is present as well as those areas in which it is absent.

The invention also differs from the previous methods in that fluorescence is created by altering only the outer layer of a parylene coating leaving the bulk of the parylene in its original state. Hence, the fluorescence is of the type wherein the brightness is substantially independent of the parylene film thickness.

The process comprises the steps of:

(a) exposing the parylene coating on said article to an active plasma under conditions and for a period of time sufficient to induce fluorescence in said parylene, (b) exposing the parylene coating to light of a wavelength suitable for the detection of fluorescence in said coating, and (c) observing those areas of said article wherein fluorescence is present or absent.

The method of the present invention provides a unique method for inducing fluorescence in parylene films and coatings which can then be used for quality control purposes. The method is useful in determining whether parylene which has been deposited on an article covers those areas which were intended to be covered and has not leaked onto those areas which should not be covered.

The present invention is also useful for the identification and authentification of articles such as negotiable instruments, stock certificates, credit cards, passports, and the like. By depositing parylene on such articles and inducing fluorescence in only those areas of the parylene which conform to a predetermined configuration, the authenticity of the article can be later determined by exposing the fluorescent area to black light.

DESCRIPTION OF THE DRAWINGS

The invention will be more readily understood by reference to the following drawings wherein.

DESCRIPTION OF THE PREFERRED EMBODIMENTS

Figure 1:
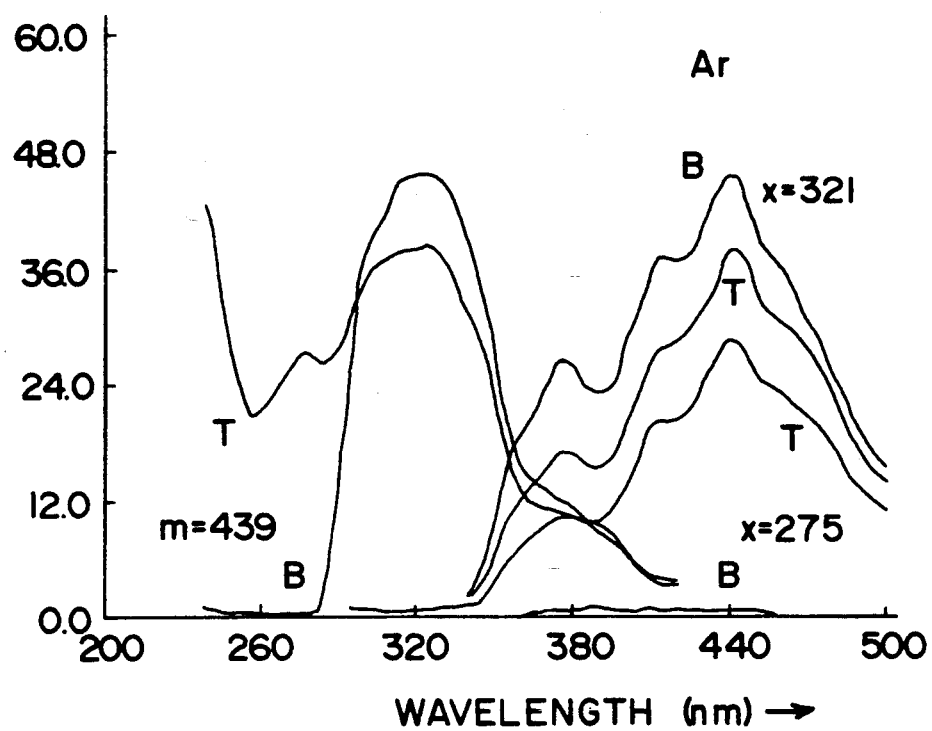
FIG. 1 is a graph showing fluorescence excitation and emission spectra of the plasma treated surface and back side of parylene C film wherein argon was utilized as the plasma gas.

As indicated above, the parylenes are very inert polymeric materials essentially insoluble in solvents Since the classical methods of polymer characterization depend on the study of solutions, many of the detailed chemical properties and characteristics remain obscure.

Whereas the observation of fluorescence in the days of the early parylene workers was a simple matter of literally seeing with the human eye whether the sample glowed under a filtered low pressure mercury lamp, or black light, such as the type commonly used by geologists to examine and classify mineral specimens, the commercial equipment and apparatus of today permits control of the spectral purity and intensity of the excitation light and allows the spectral distribution of the emitted light to be measured with great detail and sensitivity. Thus earlier reports of fluorescence were qualitative and subjective, although direct comparisons of the intensity of fluorescence would permit relative rankings. With today's equipment, not only are quantitative and qualitative comparisons of fluorescence a matter of course, but its ability to detect emitted light to which the human eye is insensitive will lead to the discovery of fluorescence in materials previously categorized as non-fluorescent.

The earliest preparations of poly-p-xylylene directly from p-xylene produced material which was described as being fluorescent. The poly-p-xylylenes as prepared by the pyrolysis of cyclo-di-p-xylylene by the method of Gorham, however, were described as essentially non fluorescent. It was concluded that the difference in fluorescence seen was the result of impurities included in the polymer which were generated under the more strenuous conditions required in preparing the polymer directly from p-xylene. It was further concluded that fluorescence was not an inherent property of pure poly-p-xylylene.

As parylene became a highly desirable coating for printed circuit assemblies, it became important to be able to impart fluorescence to the essentially non-fluorescent polymer by the addition of brighteners to facilitate inspection of the coated circuit assembly. This was accomplished by the addition of brighteners during the process of vapor deposition of the parylene coating onto an appropriate substrate. As previously mentioned, the conditions under which parylene deposition was accomplished severely limited the choice of brightener additives to a very few chemical compounds. Moreover, by adding the brighteners at the time of deposition, the resulting coatings had the brighteners distributed throughout the parylene coating and over the surfaces coated.

As previously indicated the distribution of the additives in the parylene coating varied with the greatest concentration following the line of sight from the generator output nozzle. Accordingly, the concentration of fluorescent additive varied over the substrate surfaces coated with the greater concentration along the line of sight and decreasing concentrations with increasing distance from the line of sight of the generator nozzle. However, when subjected to the appropriate light source, the entire coating fluoresced. Accordingly, it was not possible to limit the fluorescence to predetermined sites in the coating.

It was unexpectedly found, however, that certain parylenes, namely Parylene C which contains about one chlorine atom per aromatic ring, and Parylene D, which contains about two chlorine atoms per aromatic ring, could be made to fluoresce after the coating was deposited on a substrate surface. This was surprising in the light of the earlier conclusion that fluorescence was not an inherent property of the polymer. It was further surprising because it has been generalized from observations in other molecular systems that the inclusion of a heavier atom such as chlorine in a fluorescing system tends to reduce or quench the fluorescence.

In copending U.S. patent application Ser. No. 07/501,722, filed Mar. 30, 1990, and which is assigned to the same assignee as the present invention, there is disclosed and claimed a method for imparting fluorescence to parylene films and coatings by exposure of the parylene to light excitation means, such as ultra violet light of the proper wavelength. In that method fluorophores (a molecule or molecular fragment capable of producing fluorescence) are induced throughout the thickness of the parylene coating.

In contrast, in the present invention fluorescence in the parylene coating is effected by exposure of the parylene to an active plasma, and therefore the present invention creates fluorophores only in the surface layer of the parylene film or coating. Accordingly, the method of the present invention leaves the bulk of the parylene in its original state. Since plasma induced fluorescence results from fluorophores located only in the surface layer, it can be completely removed by etching away the outermost layer of the parylene coating containing the fluorophores. This may be desirable when the parylene has been deposited in areas in which fluorescence patterning must be changed. The use of an oxygen plasma is particularly effective in removing a parylene coating. It can be controlled to the extent that only the outermost layer of the parylene is etched away and accordingly, the bulk of the parylene coating remains in its original state but without the fluorescent outer layer.

In practice, the present invention utilizes known techniques for generating a low pressure plasma from available equipment. Plasmas can be generated using electric fields of a variety of frequencies, from microwaves down to zero (a DC plasma) including radio frequencies. Although various types of equipment can be used, one type of apparatus uses an RF induction coil to generate the plasma that surrounds the substrate to be treated. The vacuum pump establishes a low background pressure before any gas is admitted into the work chamber. Once started, the gas flows continuously from the supply via flow regulating controls. At the correct pressure level, RF power from the generator, tuned into the plasma load by the matching transformer network, transfers about 300 W from the 50 ohm generator output to the several thousand of ohms of impedance that the plasma load may represent.

The following is a description of an apparatus embodiment suitable for the practice of this invention: the apparatus may consist of a quartz or metal chamber having a 10 inch diameter barrel and 20 inches long evacuated to a low pressure, preferably less than about 0.5 torr. A gas flow may be introduced to raise the pressure within the chamber to about 1-2 torr. The RF power supply operates at 13.56 MHz and can be used to variable supply power from 0-1500 watts activating the plasma. While the pressure at which a plasma can be generated is usually less than about 100 torr, it is preferred to operate at a pressure between about 0.10 and about 5 torr, and most preferred between about 0.20 and about 2 torr.

Gases suitable for creating plasmas include gases such as oxygen, nitrogen, argon, helium, neon, xenon, $CF_4$ and the like and mixtures thereof. The preferred plasma gases for use in creation of fluorescence in parylene are argon and helium. It was noted, however, that attempts to render parylene coated surfaces fluorescent by treatment with an oxygen plasma resulted in no fluorescence at all. Even when mixtures of gases were employed, such as 90 percent argon and 10 percent oxygen, no fluorescence was observed in the plasma treated parylene.

In general, it has been noted that optimum fluorescence is achieved if the plasma conditions for inducing fluorescence are controlled within certain limits. For example, the gas flow in the plasma treatment chamber should be from about 100 to about 1000 std $cm^3/m$ and more preferably from about 200 to about 400 std $cm^3/m$. The pressure within the chamber should also be from about 0.10 torr to about 5 torr, and more preferably from about 0.20 to about 2 torr. The temperature at which the parylene films or coatings are rendered fluorescent should also be from about 25° C. to about 200° C., and more preferably from about 50° C. to about 100° C.

In practice, it has been observed that exposure of the parylene coating to the active plasma can range from about 1 second to 1 hour, and preferably from about 5 seconds to five minutes. Depending primarily upon the intensity of the source, the particular exposure time can vary above and below these ranges. It has been observed that the best results are achieved within the indicated ranges.

In order to demonstrate that UV light generated within the plasma plays no direct role in creating this type of fluorescence in parylene coatings, as is the case in the aforementioned copending application, experiment was conducted in a different type of apparatus. This apparatus contained a pair of capacitor plates to generate the plasma for treating substrates. In addition, this apparatus contains a perforated aluminum cylinder that prevents ultraviolet radiation from penetrating the space within the cylinder. It was therefore clearly shown that ultraviolet radiation was not responsible for the fluorescence.

While fluorescent sites are optimally created in parylene using the method of the present invention, after being created, these same fluorescent sites are optimally observed or read out using ultraviolet excitation radiation of wavelength about 321 nm. It has been found that the maximum fluorescence intensity is at a wavelength of 371 nm, which is a type of light to which the human eye is insensitive. Even when the readout excitation photons are monochromatic, in the optimal case purely at 321 nm, the emitted photons have wavelengths extending from 330 nm to beyond 500 nm. It is the emitted wavelengths longer than about 390 nm to which the human eye begins to have appreciable sensitivity.

In a simplest form, a "black light" is used as the readout excitation means in surroundings of subdued illumination. In the "black light", the output of a small mercury lamp is filtered to remove most radiation to which the human eye is sensitive, passing the ultraviolet portion of its output as the readout excitation. The fluorescent site patterns within Parylene C or Parylene D coatings or films which have been previously exposed to the plasma treatment will be seen as a brightly glowing fluorescence. The brightness of the readout fluorescence will be directly proportional to the intensity of the readout excitation reaching the surface of the parylene coating, which in turn depends directly on the intensity of the black light source, and inversely with the square of the distance between the black light source and the fluorescing sites in the parylene coating.

In a more efficient form, monochromatic light of about 321 nm can be employed which is extracted from an appropriate source using filters or monochromaters as necessary, and directed upon a parylene coating which has previously been rendered fluorescent. Light emitted from the induced fluorescence is filtered or monochromated to reject specular reflection of the 321 nm excitation and passed to a photoelectric detection system which responds well to light in the general region of 370 nm in the near ultraviolet.

The novelty of the present invention resides, in part, in inducing uniform fluorescence in parylene coatings by plasma treatment and using the fluorescence to determine whether the substrate which has been coated with parylene is fully coated or whether there are any holidays or uncoated regions. Additionally, the invention is also directed to the use of the plasma treatment to induce fluorescence in just those portions of the parylene coating where fluorescence is desired. For inducing fluorescence in parylene coatings wherein the site is relatively large, this can be easily accomplished by masking those portions where fluorescence is not desired.

Thus, for many applications such as the identification and authentification of articles having a portion thereof coated with parylene, placing a simple mask over the coating will be sufficient. Exposure of the unmasked areas can then be made to the active plasma means.

In practice, the process of the present invention can be utilized for a wide variety of applications where it is desired to impart and later retrieve data such as identifying marks, symbols, letters, words or digital data, and the like, to articles coated in whole or in part with parylene. Such identifying or authenticating data can be as simple as a single mark or symbol imparted to parylene coated articles. Alternatively, identifying data can be of a more complex nature, such as logos, letters, words and the like, imparted to negotiable instruments including currency, bank notes, stock and bond certificates, and the like. Credit cards, passports and other articles, can also have identifying marks in the form of fluorescent sites created on the article for the purposes of identification or authentication. When exposed to a proper fluorescence detecting device, the data which has been imparted to the parylene coating and is not visible to the naked eye, becomes readable.

Articles such as tapes, disks and other digital memory can also be coated with parylene and fluorescent sites induced in accordance with the teachings of the present invention for the storage and retrieval of useful information in digital form.

In practice, all that is needed is a thin layer of parylene, whether or not it remains attached to the substrate on which it was deposited to provide sites for imparting fluorescence. Deposition of the parylene coating on articles is effected by methods known in the art.

The following examples are illustrative of the present invention.

EXAMPLE 1

A substrate material comprised of aluminum and having dimensions of approximately 0.5 inches by 2 inches which was coated with parylene C by known methods to provide a film thickness of approximately 0.5 mils. The coated substrate was then treated with an argon plasma for approximately 2 minutes. A Branson-/IPC series 400 (Haywood, Calif.) was employed to provide the plasma. The R.F. power supply operated at 13.56 MHz with an input power of 50 watts. The chamber was 10 inches in diameter and 20 inches long. Cylinder grade argon was used with a flow rate of about 200 std $cm^3/m$ and a chamber pressure of about 1.0 torr.

The coated substrate was treated with argon plasma at 50 watts for about 2 minutes. Upon excitation of the treated parylene by black light, the parylene coating fluoresced.

EXAMPLE 2

The experiment set forth in Example 1 was repeated except that treatment was with the argon gas plasma at 500 watts for 5 minutes. Upon excitation of the treated parylene by black light the coating fluoresced brilliantly.

EXAMPLE 3

The experiment set forth in Examples 1 and 2 was repeated except that treatment was with helium gas plasma in place of the argon. Upon excitation of the treated parylene by black light the coating fluoresced brilliantly.

EXAMPLE 4

The experiment set forth in Examples 1 and 2 was repeated except that oxygen gas plasma was used in place of the argon. Upon excitation of the treated parylene by black light no fluorescence was observed.

EXAMPLE 5

The experiment set forth in Examples 1 and 2 was repeated using a mixture of 90 percent by volume of argon and 10 percent by volume of oxygen. Upon excitation of the treated parylene by black light no fluorescence was noted.

EXAMPLE 6

Four samples of parylene C of about 25 micrometers'0 thickness were prepared on separate substrates of clean window glass by the vapor deposition polymerization process. The samples still attached to the glass, were exposed to plasmas of four different gases: argon, helium, carbon tetrafluoride and oxygen. The conditions of plasma treatment were five minutes at a pressure of one torr using 200 Watts of input RF power. The plasma exposed surfaces were marked with a felt tipped pen for identification purposes. Then the parylene films were separated from the glass. Samples representing the plasma treated side and the back side were cut from adjacent portions of the films, and mounted in labelled sample holders.

The samples were examined using a Perkin-Elmer Luminescence Spectrometer, model LS5B, equipped with a front surface accessory. A 2% neutral density filter attenuated the excitation beam, and other spectrometer settings were excitation slit=00, emission slit=5 nm, scan speed=60 nm/min, and response=4.

In FIGS. 1–4, for each plasma gas, the pairs of luminescence spectra are presented, labelled T for plasma treated side, and B for back side, or the side against the window glass during plasma exposure. For each gas, one pair of excitation spectra, labelled m=xxx, where xxx is the fixed setting of the emission monochromater in nm while the excitation monochromater is scanned, and two pairs of emission spectra, labelled x=yyy, where yyy is the fixed setting of the excitation monochromater in nm while the emission monochromater is scanned. The excitation wavelengths of 275 nm and 321 nm were chosen because, while light of 321 nm can pass through the entire 25 micrometer thickness of the parylene C film with minor loss, light at 275 nm is largely absorbed after passing through only one micrometer of the parylene C. Thus, the x=321 scans excite fluorophores throughout the thickness of the 25 micrometer film, while the x=275 scans excite only fluorophores residing in the outermost micrometer of the film.

Figure 4:
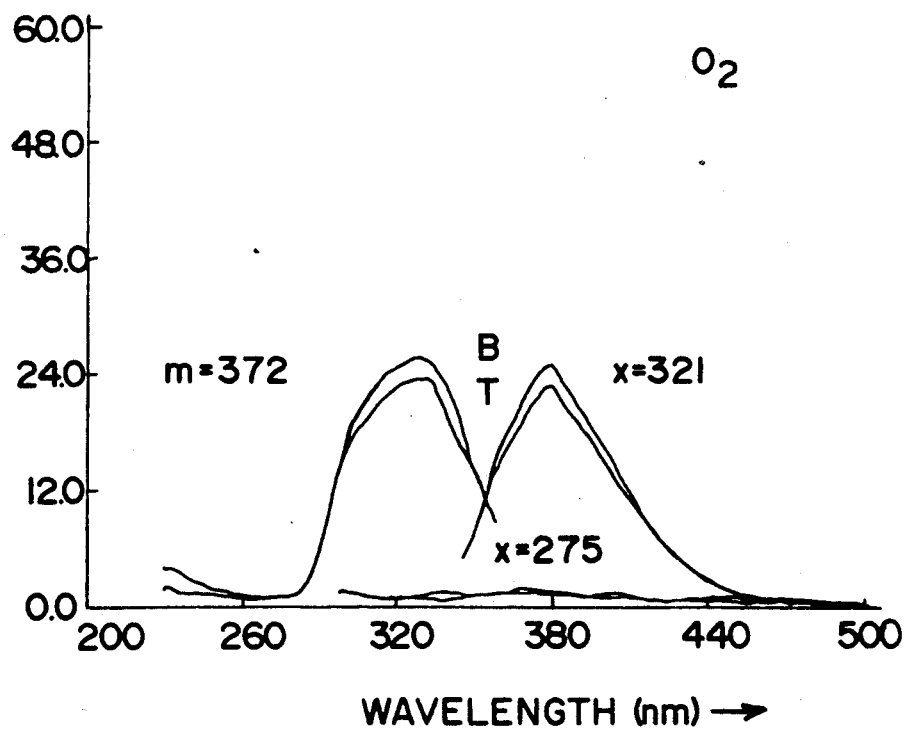
FIG. 4 is a graph showing fluorescence excitation and emission spectra of the plasma treated surface and back side of parylene C film wherein oxygen was utilized as the plasma gas.

In the oxygen plasma treated sample, FIG. 4, the only fluorescence seen is that of the congenital fluorophores, i.e., those fluorophores known to be present in parylene C throughout its thickness from the time it is prepared by vapor deposition polymerization. There is virtually no difference between the treated side and the back side. Excitation at 275 nm produces little fluorescence at all.

Figure 2:
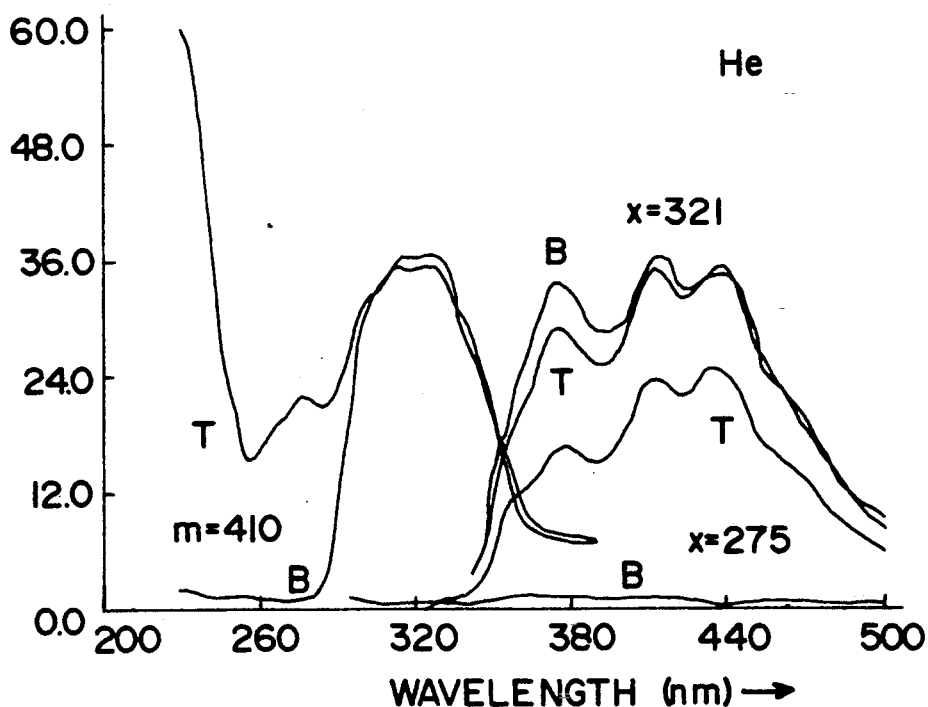
FIG. 2 is a graph showing fluorescence excitation and emission spectra of the plasma treated surface and back side of parylene C film wherein helium was utilized as the plasma gas.
Figure 3:
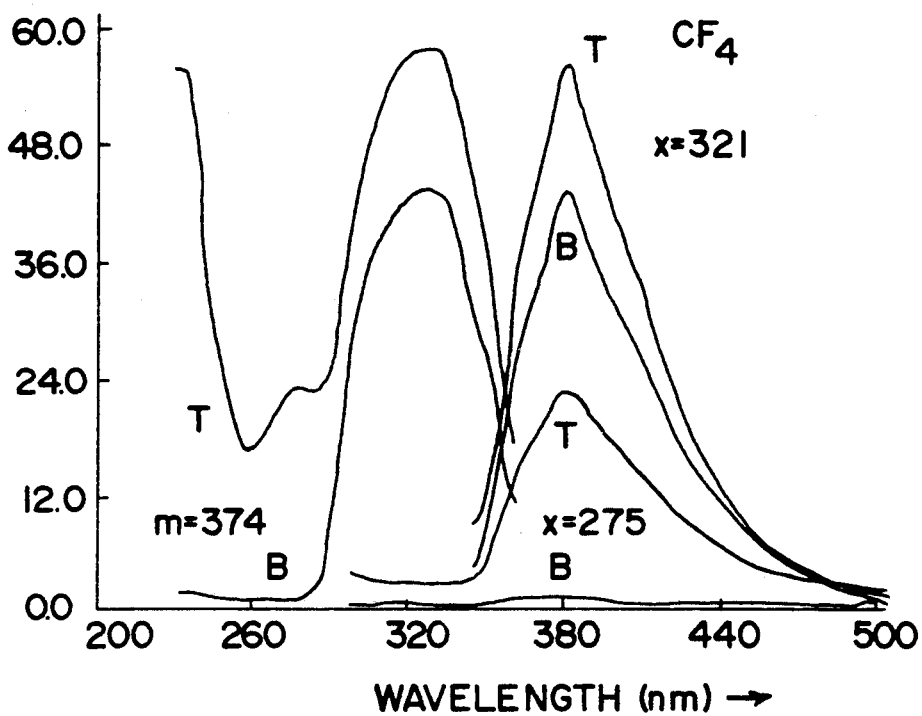
FIG. 3 is a graph showing fluorescence excitation and emission spectra of the plasma treated surface and back side of parylene C film wherein carbon tetrafluoride was utilized as the plasma gas.

The other three plasma gases, as shown in FIG. 1-3, give results similar to one another in the following respects. The treated side and the back side in general are different. This difference is more pronounced when the excitation is at 275 nm, the wavelength which can only excite fluorophors within the first micrometer of the surface of parylene C. While the back sides give little response in the x=275 emission scan, the treated sides fluoresce brightly, testifying to the presence of fluorophores located near the surface of the plasma treated side. This same effect of surface fluorescence is seen in the excitation (m=xxx) scans below about 280 nm. The results observed in the x=321 nm emission scans is a superposition of surface fluorescence and congenital fluorescence, the surface fluorescence seen in the back side being excited by light somewhat attenuated after having passed through the 25 micrometer thickness of the parylene C film before reaching the surface fluorophores.

Argon, helium and carbon tetrafluoride plasma treatment results differ significantly in the amount of long wavelength light emitted. The human eye becomes increasingly sensitive to light above about 400 nm. Using these results to select among these plasma treatment gases for visual quality control inspection, the order of preference is argon > helium > carbon tetrafluoride.

EXAMPLE 7

Paryelne C coated coupons which had previously been rendered fluorescent by exposure to an inert gas plasma were subjected to a fluorescence removal treatment. This treatment consisted of exposing the fluorescent parylene C surfaces to an oxygen plasma (100 watts, 0.5 torr) for two minutes and resulted in the complete removal of the fluorescence which had been previously imparted to the parylene C surfaces by the inert gas plasma. Separate calibration experiments in which parylene C coatings of known thickness were completely removed in an oxygen plasma generated in the same plasma apparatus at the same operation conditions established parylene C oxygen strip rates of 2 to 5 nm per minute. The fluorescent layer imparted by the inert gas plasma is therefore estimated to be 4 to 10 nm thick from the time required for its removal.

EXAMPLE 8

During the parylene C coating of electronic assemblies, those portions which are intended not to be coated are masked off. However, parylene C is quite pervasive, and will form coatings of reduced thickness under the masking means if the masking means is insufficiently effective. Since even a very thin layer of parylene C on a contact finger will interfere with the proper electrical function of the part, the following quality control procedure has been found useful for inspecting parylene C coated parts:

To determine whether parylene C has leaked into a masked connector, the parylene coated assembly is first masked off except for the connector to be tested. The assembly is subjected to a fluorescence generation cycle in argon plasma (70 watts at 0.5 torr) for two minutes. The connector area is then inspected under black light illumination to determine whether parylene C is present inside the connector on critical surfaces. A thin layer of parylene C on a critical surface makes its presence known with a bright fluorescence.

EXAMPLE 9

This example illustrates the use of the method of the present invention for identifying and/or authenticating currency. In this example, new United States one dollar bills are placed in a parylene generator and coated with 340 nm of parylene C. Some of the bills are masked or templated with right triangle heavy duty paper forms covering about one half of the bills. Other bills are templated with letters, stars, washers and perforated plates. The bills are then exposed to an argon plasma under the conditions set forth in Example 2 to induce fluorescence. The coated and exposed bills appeared normal to the eye. However, upon examination under black light, the bills glow brilliantly in exact replication of the templates used. Although the covered areas appeared dark, the uncovered areas glow brilliantly.

Although the invention has been illustrated by the preceding examples, it is not to be construed as being limited to the materials employed therein, but rather, the invention is directed to the generic area as herein disclosed. Various modifications and embodiments thereof can be made without departing form the spirit or scope thereof.

What is claimed is:

1. A method for determining whether an article which has been coated with a thin transparent layer of parylene by a vapor deposition method contains parylene on those areas intended to be coated, which comprises the steps of:

(a) exposing the parylene coating on said article to an active plasma generated at a power level of up to about 1500 watts under conditions and for a period of time sufficient to induce fluorescence in the surface layer of said parylene, (b) exposing the parylene coating to light of a wavelength suitable for the detection of fluorescence in said coating, and (c) observing those areas of said article wherein fluorescence is present or absent.

2. The method of claim 1 wherein said active plasma uses an inert gas containing less than 10 percent by volume of oxygen.

3. The method of claim 2 wherein said inert gas is argon.

4. The method of claim 2 wherein said inert gas is helium.

5. The method of claim 2 wherein said inert gas is carbon tetrafluoride.

6. The method of claim 1 wherein said fluorescence is induced by said active plasma at a pressure of from about 0.10 to about 5 torr.

7. The method of claim 1 wherein said fluorescence is induced by said active plasma at a pressure of from about 0.20 to about 2 torr.

8. The method of claim 1 wherein said fluorescence is induced by said active plasma at a gas flow of from about 100 to about 1000 std cm$^3$/m.

9. The method of claim 1 wherein said fluorescence is induced by said active plasma at gas flow of from about 200 to about 400 std cm$^3$/m.

10. The method of claim 1 wherein said fluorescence is induced by said active plasma at a temperature of from about 25° C. to about 200° C.

11. The method of claim 1 wherein said fluorescence is induced by said active plasma at a temperature of from about 50° C. to about 100° C.

12. The method of claim 1 wherein said parylene is parylene C.

13. The method of claim 1 wherein said parylene is parylene D.

14. The method of claim 1 wherein said active plasma is generated at a power level of from about 50 to 1500 watts.

15. The method of claim 1 wherein said fluorescence is substantially included only in about the first micrometer of the surface layer of said parylene.

16. A method for creating selective sites of fluorescence in articles comprised in whole or in part of parylene, which comprises the steps of:
  1) shielding with shielding means, those portions of parylene in which fluorescent sites are not desired,
  2) exposing the remainder of the parylene to an active plasma generated at a power level of up to about 1500 watts capable of inducing fluorescent sites in the surface layer of said parylene under conditions and for a period of time sufficient to create such sites, and
  3) thereafter removing the shielding means.

17. The method of claim 16 wherein said active plasma uses an inert gas containing less than 10 percent by volume of oxygen.

18. The method of claim 17 wherein said inert gas is argon.

19. The method of claim 17 wherein said inert gas is helium.

20. The method of claim 16 wherein said fluorescence is induced by said active plasma at a pressure of from about 0.2 to about 5 torr.

21. The method of claim 16 wherein said fluorescence is induced by said active plasma at a pressure of from about 0.20 to about 2 torr.

22. The method of claim 16 wherein said fluorescence is induced by said active plasma at a gas flow of from about 100 to about 1000 std $cm^3/m$.

23. The method of claim 16 wherein said fluorescence is induced by said active plasma at gas flow of from about 200 to about 400 std $cm^3/m$.

24. The method of claim 16 wherein said fluorescence is induced by said active plasma at a temperature of from about 25° C. to about 200° C.

25. The method of claim 16 wherein said fluorescence is induced by said active plasma at a temperature of from about 50° C. to about 100° C.

26. The method of claim 16 wherein said parylene is parylene C.

27. The method of claim 16 wherein said parylene is parylene D.

28. A method of identifying and insuring the authenticity of an article which comprises the steps of:
  1) coating at least a portion of said article with parylene;
  2) shielding with shielding means of a particular configuration, those portions of the parylene coating in which fluorescent sites are not desirable;
  3) exposing the remainder of the parylene to active plasma generated at a power level of up to about 1500 watts capable of inducing fluorescent sites in the surface layer of said parylene under conditions and for a period of time sufficient to create such sites;
  4) removing the shielding means; and
  5) exposing the article to light of a wavelength suitable for the detection of the fluorescent sites to confirm the presence of the predetermined configuration.

* * * * *